United States Patent [19]

Ito

[11] Patent Number: 5,063,025
[45] Date of Patent: Nov. 5, 1991

[54] ANALYTICAL MICROSYRINGE WITH A SUPERELASTIC PLUNGER

[75] Inventor: Tatsuharu Ito, Tokyo, Japan
[73] Assignee: Ito Corporation, Shizuoka, Japan
[21] Appl. No.: 481,568
[22] Filed: Feb. 20, 1990
[51] Int. Cl.⁵ .......................... B01L 3/02; G01N 1/02; A61M 5/315
[52] U.S. Cl. .................................. 422/100; 604/218; 73/864.16
[58] Field of Search ...................... 422/100; 73/864.13, 73/864.16, 864.17, 864.18; 604/218

[56] References Cited
U.S. PATENT DOCUMENTS
3,232,117 2/1966 Gilmont ........................... 73/864.13
3,537,453 11/1970 Drummond et al. ............ 73/864.13

Primary Examiner—David L. Lacey
Assistant Examiner—Jan M. Ludlow
Attorney, Agent, or Firm—Wenderoth, Lind & Ponack

[57] ABSTRACT

An analytical microsyringe includes a syringe body, an injection needle fixed to the inner surface at one end of the syringe body, a linear plunger formed of superelastic wire and a knob integrally fixed to the rear end of the linear plunger. The linear plunger has the front end thereof formed to have a diameter large enough to tightly and slidably contact the inner surface of the syringe body and a portion thereof other than the large-diameter front end formed to have a smaller diameter and keep clear of the inner surface of the syringe body.

8 Claims, 5 Drawing Sheets

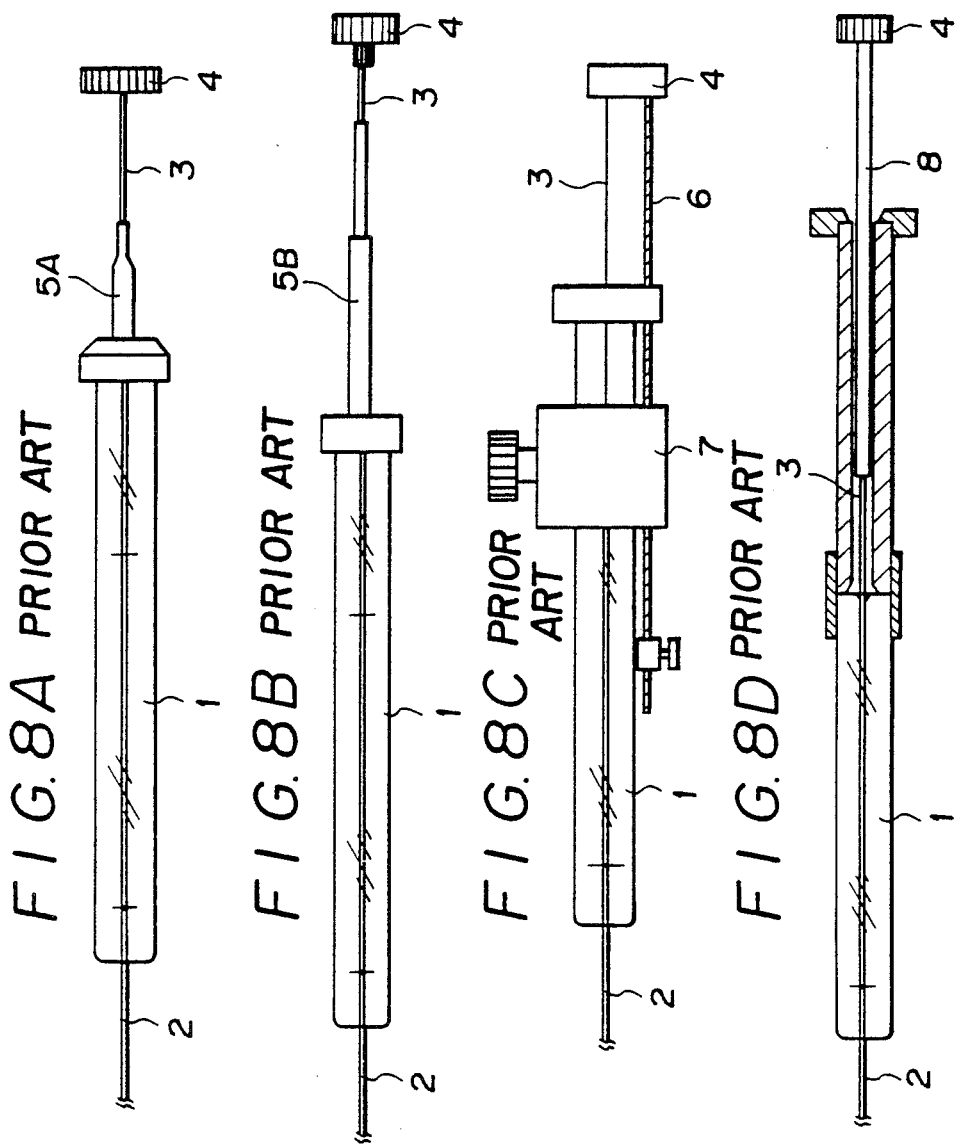

ANALYTICAL MICROSYRINGE WITH A SUPERELASTIC PLUNGER

BACKGROUND OF THE INVENTION AND PRIOR ART STATEMENT

This invention relates to an analytical microsyringe usable as in gas chromatography and liquid chromatography.

As illustrated in FIG. 7, the microsyringe of this kind generally comprises a syringe body 1 made of glass, an injection needle 2 fixed to the leading end part of the syringe body 1, a linear metallic plunger 3 slidable inside the syringe body 1 and a knob 4 mounted on the rear end of the plunger 3. It is used in injecting a stated amount of a gaseous or liquid sample into an analytical apparatus.

For the purpose of enabling a minute amount of the sample to be introduced into and discharged out of the syringe body 1, the microsyringe is configured so as to produce close sliding engagement between the inner surface of the syringe body 1 and the outer surface of the plunger 3.

Since the prior art microsyringe uses the plunger 3 formed of stainless steel wire or piano wire of small elastic strain, it has a disadvantage that the plunger 3 bends and sustains permanent deformation during the course of use even when the microsyringe is handled fully attentively.

In the case of a microsyringe having a volume of 5-$\mu$l and having a plunger 3 which has a diameter of 0.370 mm and a stroke of 46.5 mm, for example, since the diameter of the plunger 3 is very small, it sustains a bend quite naturally in the course of use. When the plunger 3 is bent even slightly, the state of close sliding engagement no longer exists between the outer surface of the plunger 3 and the inner surface of a syringe body 1. The permanent deformation of the plunger 3 mentioned above prohibits a gaseous or liquid sample from being introduced into and discharged out of the syringe body 1 precisely in a minute amount and spoils the function of the microsyringe. For this reason, the microsyringes of the latest development are provided with various means for protecting the plunger 3 against such a bend, as illustrated in FIGS. 8A to 8D.

A prior art microsyringe illustrated in FIG. 8A is provided with a tubular protector 5A made of Teflon (polytetrafluroethylene) in stated dimensions and disposed on the side of the plunger insertion mouth of a syringe body 1, so that the guiding action of the tubular protector 5A may enable the plunger 3 to slide closely on the syringe body 1. A tubular protector 5B of another prior art microsyringe illustrated in FIG. 8B is of a telescopic structure.

In still another prior art microsyringe illustrated in FIG. 8C, a guide bar 6 is attached to a knob 4 in such a manner as to extend in parallel to a plunger 3 and this guide bar 6 is slidably supported in place by a holder 7 disposed on a syringe body 1, so that the slide of the guide bar 6 against the holder 7 may enable the plunger 3 to slide on the syringe body 1.

FIG. 8D illustrates yet another prior art microsyringe which has a reinforcing pipe 8 set around a plunger 3 so that the reinforcing action of the reinforcing pipe 8 may enable the plunger 3 to slide on a syringe body 1.

Although the conventional means for preventing the plunger from bending are more or less different in structure from one another, they are invariably incapable of completely preventing the plunger 3 of stainless steel wire from sustaining permanent deformation due to bending. In addition, the provision of such bend-preventing means only goes to add to the cost of the microsyringe itself but fails to fully accomplish the object thereof.

In the conventional microsyringes, since the inner surface of the syringe body 1 and the outer surface of the plunger 3 are ground against each other throughout their entire surfaces, the rubbing forcibly scrapes the outer surface of the plunger 3 or the inner surface of the syringe body 1 and gives rise to ground powder between the closely opposed surfaces of the two members, with the result that smoothness of the slide of the plunger 3 will frequently be impaired.

OBJECT AND SUMMARY OF THE INVENTION

The main object of the present invention is to provide an analytical microsyringe free from all of the various problems encountered by the conventional microsyringes described above.

To attain the object described above, according to the present invention there is provided an analytical microsyringe comprising a syringe body having an inner surface, an injection needle fixed to the inner surface of the syringe body at one end of the syringe body, a linear plunger formed of superelastic wire and having one end thereof formed to have a diameter large enough to tightly and slidably contact the inner surface of the syringe body and a portion other than the large-diameter end of the linear plunger formed to have a smaller diameter and keep clear of the inner surface of the syringe body, and a knob integrally fixed to the other end of the linear plunger.

The above and other objects, characteristic features and advantages of the present invention will become more apparent to those skilled in the art as the disclosure is made in the following description of preferred embodiments of the invention, as illustrated in the accompanying drawings.

BRIEF DESCRIPTION OF THE DRAWINGS

FIG. 8A is a front view illustrating another prior art microsyringe provided with bend-preventing means.

FIG. 8B is a front view illustrating still another prior art microsyringe provided with different bend-preventing means.

FIG. 8C is a front view illustrating yet another prior art microsyringe provided with further different bend-preventing means.

FIG. 8D is a front view illustrating a further prior art microsyringe provided with still further different bend-preventing means.

DETAILED DESCRIPTION OF THE PREFERRED EMBODIMENTS

Now, the present invention will be described specifically hereinbelow with reference to the embodiments illustrated in the accompanying drawings.

Figure 1:
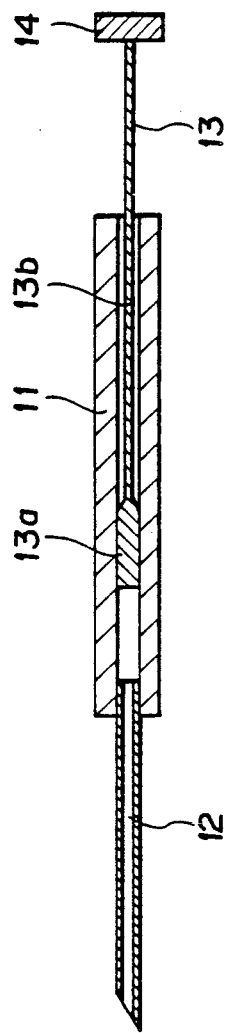
FIG. 1 is a cross section illustrating one embodiment of the analytical microsyringe according to the present invention.

FIG. 1 illustrates one embodiment of the analytical microsyringe according to the present invention. This analytical microsyringe comprises a syringe body 11 formed of borosilicate glass or hard glass, an injection needle 12 fixed to the inner surface at one end of the syringe body 11 with adhesive agent or by any other fixing means, a linear plunger 13 slidable inside the syringe body 11, and a knob 14 fixed integrally to the rear end of the linear plunger 13.

The linear plunger 13 is formed of superelastic wire which can be made of a superelastic alloy or a superelastic amorphous alloy. A superelastic alloy is produced by molding a Ni-Ti alloy in a linear shape circular in cross section and then subjecting the molding alloy to heat treatment for imparting superelasticity. The linear plunger 13 has a large-diameter portion 13a constituting the front end and a small-diameter portion 13b smaller by approximately 0.001 to 0.5 mm than the large-diameter portion 13a and consitituting the remaining part of the linear plunger 13. The large-diameter portion 13a is adapted to tightly contact the inner surface of the syringe body 11, whereas the small-diameter portion 13b keeps clear of the inner surface of the syringe body 11.

Figure 2:
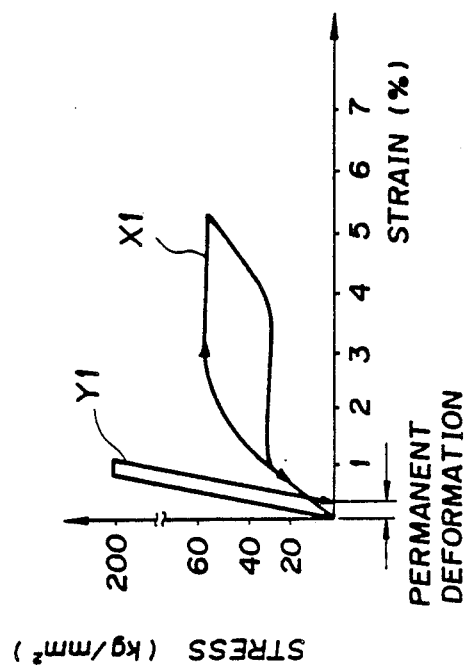
FIG. 2 is a graph illustrating stress-strain curves of superelastic wire and stainless steel wire.

FIG. 2 illustrates the strain-stress curves of superelastic wire X1 and stainless steel wire Y1 and indicates that while the stainless steel wire Y1 has sustained permanent deformation under strain of about 1%, the superelastic wire X1 has avoided sustaining any permanent deformation even under strain exceeding 5% and has restored to its original linear shape after release of load.

Figure 3:
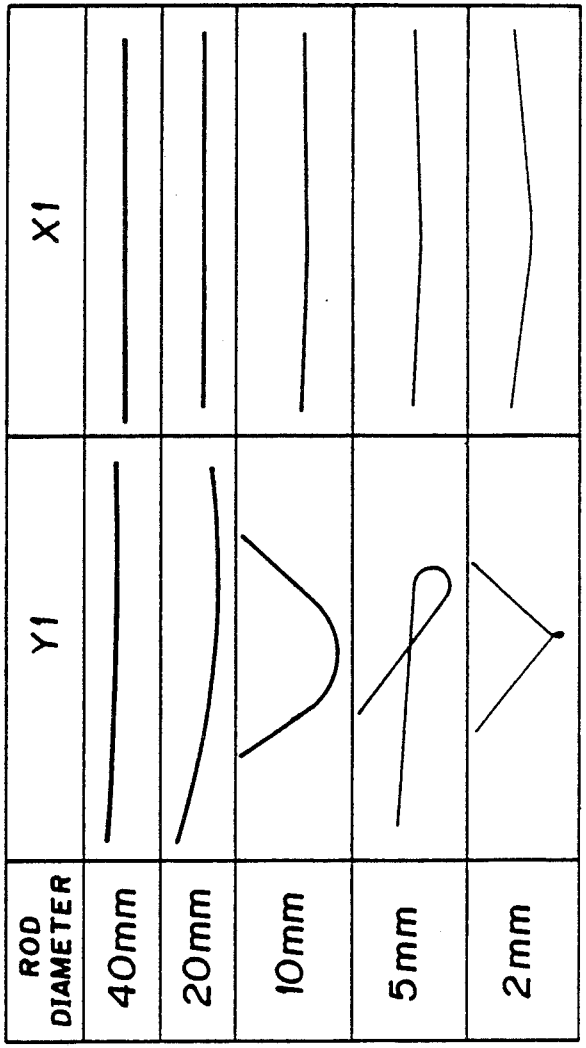
FIG. 3 is a diagram illustrating results of a bending test performed on superelastic wire and stainless steel wire.

An experiment was conducted for the purpose of comparing the degree of deformation of the superelastic wire X1 with that of the stainless steel wire Y1 by following the procedures of winding each of the stainless steel wire Y1 and superelastic wire X1 one circle around several round bars differing in diameter and pulling the opposite ends of each wire for about ten minutes. The results are shown in FIG. 3 from which it is clearly noted that the stainless steel wire Y1 showed no notable deformation to a round bar 40 mm in outside diameter and showed gradually larger degrees of deformation to round bars having sequentially decreasing outside diameters of 20 mm, 10 mm, 5 mm and 2 mm, whereas the superelastic wire X1 showed virtually no deformation to round bars having outside diameters of 40 mm, 20 mm, 10 mm and 5 mm and showed a slight degree of deformation only to a round bar having the smallest outside diameter of 2 mm.

From the results of the experiment described above, it is found that the superelastic wire X1 has 5 to 7 times as high elastic strain as the stainless steel wire Y1. Since the linear plunger 13 of the embodiment is formed of the superelastic wire X1, the analytical microsyringe obviates the necessity for the heretofore indispensable bend-preventing means and precludes the possibility of the linear plunger 13 being bent and consequently sustaining permanent deformation during the course of normal use.

It has been further demonstrated that the superelastic wire X1 is superior to the stainless steel wire Y1 in terms of resistance to chemicals.

Figure 4A:
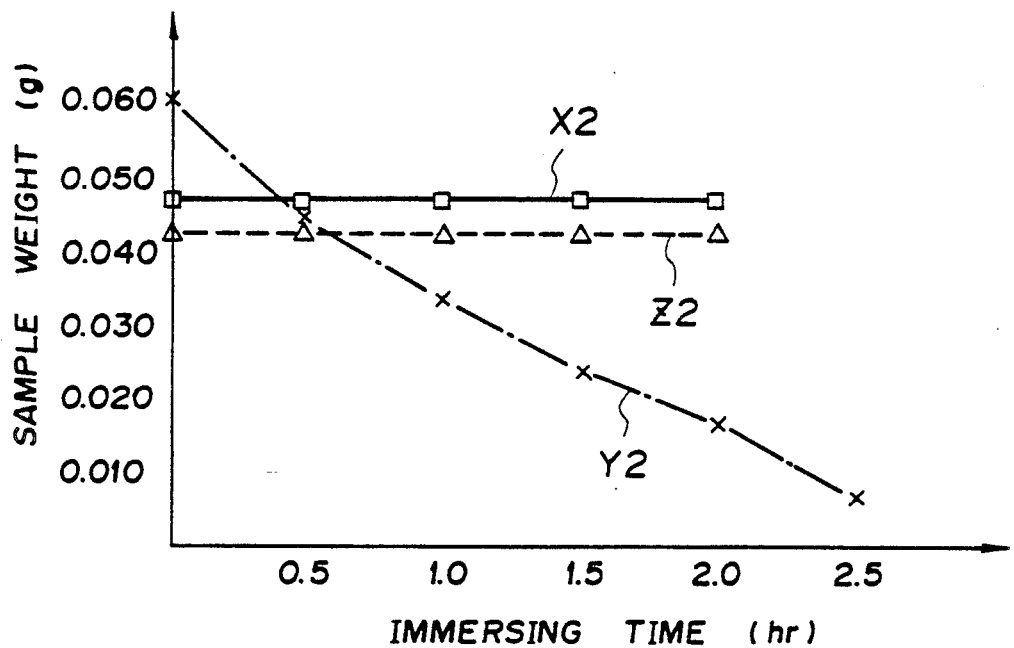
FIG. 4A is a graph illustrating results of a test for resistance to chemicals performed on samples of superelastic alloy wire, stainless steel wire and amorphous alloy wire.
Figure 4B:
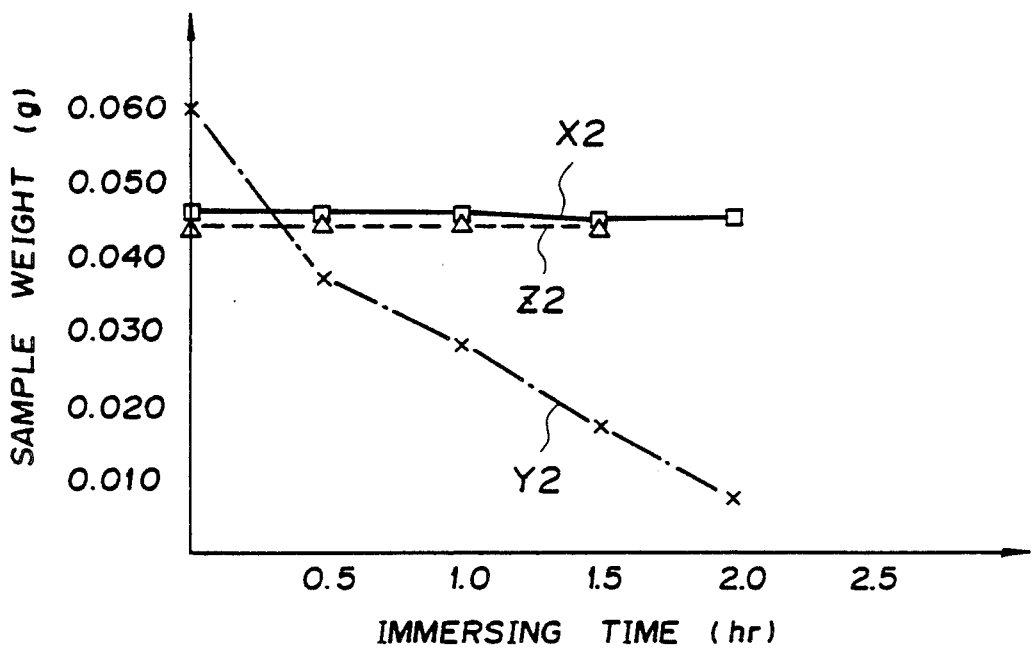
FIG. 4B is a graph illustrating results of another test for resistance to chemicals performed on samples of superelastic alloy wire, stainless steel wire and amorphous alloy wire.

FIG. 4A is a graph showing the results of an experiment comprising the steps of immersing a superelastic alloy sample X2, a stainless steel sample Y2 and superelastic amorphous alloy sample Z2 together in a boiling aqueous 5% hydrochloric acid solution and measuring changes of weight occurring in the samples in consequence of corrosion. It is clearly noted from the graph of FIG. 4A that while the stainless steel sample Y2 lost weight proportionately to the length of time of immersion in the solution, the superelastic alloy sample X2 and superelastic amorphous alloy sample Z2 showed virtually no change of weight without reference to the time of immersion in the solution. FIG. 4B is a graph showing the results of an experiment comprising the steps of immersing the same samples in a boiling aqueous 5% sulfuric acid solution and measuring changes in weight. It is clearly noted from the graph of FIG. 4B that while the stainless steel sample Y2 lost weight proportionately to the elapse time of immersion in the solution, the superelastic alloy sample X2 and superelastic amorphous alloy sample Z2 showed virtually no change of weight without reference to the time of immersion in the solution.

Thus, it has been confirmed that the plunger 13 made of superelastic wire in the present embodiment not only avoids sustaining any permanent deformation but also excels in resistance to chemicals.

The conventional microsyringe has the plunger thereof formed of stainless steel wire. When the conventional microsyringe is used in handling such a non-oxidizable acid as hydrochloric acid or sulfuric acid, therefore, it cannot withstand this use very long because the oxide coating of the plunger is destroyed or corroded by the acid. In contrast, the microsyringe of the present embodiment using a plunger made of a superelastic alloy or amorphous alloy can be safely used in handling the aforementioned non-oxidizable acid.

Furthermore, the present embodiment, unlike the prior art microsyringe, adopts a configuration such that the plunger 13 has the large-diameter portion 13a which constitutes the front end thereof and tightly contacts the inner surface of the syringe body 11 and the small-diameter portion 13b which constitutes the remaining part thereof and keeps clear of the inner surface of the syringe body 11. Owing to this configuration, the present embodiment prevents the scraping of the outer surface of the plunger 13 and the inner surface of the syringe body 11 to the fullest possible extent and eliminates the possibility of the sliding motion of the plunger 13 being impaired.

Figure 5A:
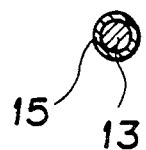
FIG. 5A is a cross section illustrating a linear plunger of a second embodiment of the analytical microsyringe according to the present invention.
Figure 5B:
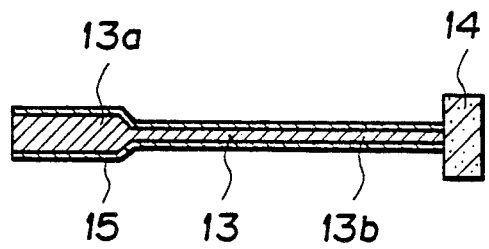
FIG. 5B is a cross section illustrating the linear plunger with a knob fixed integrally thereto.

The second embodiment of the analytical microsyringe according to the present invention will now be described. As illustrated in FIGS. 5A and 5B, the second embodiment differs from the first embodiment only in respect that a protective coating layer 15 is formed on the outer surface of the plunger 13 of superelastic wire by coating the outer surface with a thermoplastic resin such as Teflon, polyethylene or polypropylene or plating the outer surface with nickel or chromium.

In the second embodiment, therefore, the presence of the protective coating layer 15 formed on the outer surface of the plunger 13 ensures effective retention of tight contact between the opposed surfaces and warrants effective prevention of the occurrence of ground powder. Thus, the microsyringe of the second embodiment enjoying still better performance can be provided.

Figure 6A:
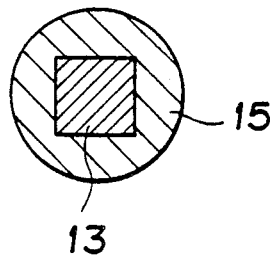
FIG. 6A is a cross section illustrating another linear plunger usable for the purpose of the present invention.
Figure 6B:
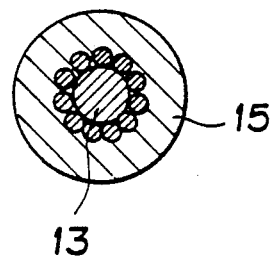
FIG. 6B is a cross section illustrating still another linear plunger usable for the purpose of the present invention.
Figure 7:
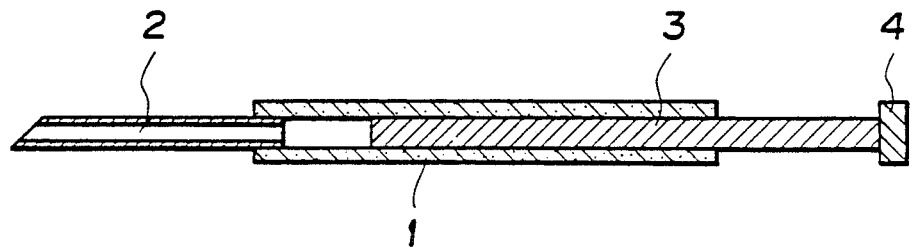
FIG. 7 is a cross section illustrating a prior art microsyringe.

Although the first and second embodiments contemplate giving the plunger 13 a circular cross section, the circularity of the cross section is not particularly critical for the present invention. For example, the plunger 13 may be given a polygonal (tetragonal, for example) cross section as shown in FIG. 6A having the protective coating layer 15 formed on the outer surface thereof. Alternatively, the plunger 13 may be made of a braided cord composed of a plurality of superelastic wires as illustrated in FIG. 6B having the protective coating layer 15 formed on the outer surface of the braided cord. Particularly in these configurations, improvement of the deformation resistance of the plunger 13 can be realized in addition to the retention of tight contact and the prevention of the occurrence of ground powder.

Owing to the adoption of the configuration described above, the microsyringe of the first embodiment of this invention which has the plunger thereof formed of superelastic wire obviates the necessity for the heretofore indispensable bend-preventing means and eliminates the possibility of the plunger being bent and consequently sustaining permanent deformation during the course of normal use. Moreover, since the plunger excels in resistance to chemicals, the microsyringe can be used in handling a non-oxidizable acid which the conventional microsyringes have been unable to handle. Furthermore, since only the large-diameter portion of the plunger is allowed to slide on the inner surface of the syringe body, the scraping of the outer surface of the plunger and the inner surface of the syringe body is prevented to the fullest possible extent and the impairment of the sliding motion of the plunger is eliminated and, at the same time, the sliding operation of the microsyringe is facilitated In the microsyringe of the second embodiment according to the present invention, the presence of the protective coating layer formed on the outer surface of the plunger ensures the effective retention of tight contact and permits the effective prevention of the occurrence of ground powder.

In the modifications of the plunger, the deformation resistance of the plunger can be adjusted.

What is claimed is:

1. An analytical microsyringe comprising:
   a syringe body having an inner surface;
   an injection needle fixed to the inner surface of said syringe body at one end of said syringe body;
   a linear plunger formed of superelastic wire and having one end thereof formed to have a diameter large enough to tightly and slidably contact the inner surface of said syringe body and a portion thereof other than the large-diameter end formed to have a smaller diameter and keep clear of the inner surface of said syringe body; and
   a knob integrally fixed to the other end of said linear plunger.

2. An analytical microsyringe according to claim 1, wherein said superelastic wire is made of a superelastic alloy.

3. An analytical microsyringe according to claim 1, wherein said superelastic wire is made of an superelastic amorphous alloy.

4. An analytical microsyringe according to claim 1, wherein said linear plunger is made of a braided cord composed of a plurality of superelastic wires.

5. An analytical microsyringe according to claim 1, wherein said linear plunger has an outer surface thereof formed with a protective coating layer.

6. An analytical microsyringe according to claim 5, wherein said protective coating layer is of a thermoplastic resin coated on the outer surface of said linear plunger.

7. An analytical microsyringe according to claim 5, wherein said protective coating layer is of nickel or chromium plated on the outer surface of said linear plunger.

8. An analytical microsyringe according to claim 6, wherein said thermoplastic resin is polytetrafluorethylene, polyethylene or polypropylene.

* * * * *